United States Patent
Harding et al.

(10) Patent No.: US 7,449,152 B2
(45) Date of Patent: Nov. 11, 2008

(54) METHODS AND APPARATUS FOR HANDLING COMPOUND STORAGE VESSELS

(75) Inventors: David Andrew Harding, Edgeworth (GB); James Norman Craven, Abbotsley (GB)

(73) Assignee: RTS Life Science Limited, Irlam, Manchester (GB)

( * ) Notice: Subject to any disclaimer, the term of this patent is extended or adjusted under 35 U.S.C. 154(b) by 649 days.

(21) Appl. No.: 10/874,058

(22) Filed: Jun. 22, 2004

(65) Prior Publication Data
US 2005/0026295 A1    Feb. 3, 2005

(30) Foreign Application Priority Data
Jun. 24, 2003    (GB) ................... 0314686.7

(51) Int. Cl.
*B01L 9/00* (2006.01)
(52) U.S. Cl. ......................... 422/104; 422/63
(58) Field of Classification Search ............ 422/63, 422/65, 102, 104; 156/250, 261, 510; 215/326
See application file for complete search history.

(56) References Cited

U.S. PATENT DOCUMENTS

| 4,260,581 | A | * | 4/1981 | Sakurada ................. 422/65 |
| 5,271,896 | A | * | 12/1993 | Jakubowicz et al. ......... 422/63 |
| 5,286,652 | A | | 2/1994 | James et al. |
| 6,551,833 | B1 | | 4/2003 | Lehtinen et al. |
| 2001/0002986 | A1 | | 6/2001 | Fattinger et al. |
| 2003/0106492 | A1 | | 6/2003 | Levinson et al. |

\* cited by examiner

*Primary Examiner*—Jill Warden
*Assistant Examiner*—Natalia Levkovich
(74) *Attorney, Agent, or Firm*—Amster, Rothstein & Ebenstein LLP.

(57) ABSTRACT

A method of handling a compound storage vessel (4) disposed in a cavity in a rack, the cavity having an upper and lower opening. The method includes introducing a lifting pin (15) into the cavity through the lower opening to urge the compound storage vessel upwards within the cavity. A lifting head (16) may be placed above the rack for receiving compound storage vessels.

6 Claims, 2 Drawing Sheets

METHODS AND APPARATUS FOR HANDLING COMPOUND STORAGE VESSELS

FIELD OF THE INVENTION

The present invention relates to methods and apparatus for handling compound storage vessels. Particularly, although not exclusively, the invention relates to methods and apparatus for handling microtubes, and especially a method of removing a selected microtube from a rack and a method of sealing a selected microtubes stored in a rack.

BACKGROUND TO THE INVENTION

Contemporary drug development involves the preparation and storage of a large number of compounds, and the subsequent later retrieval of selected compounds. Typically small quantities of compounds are stored in microtubes. The microtubes are stored in microtube racks which are in turn stored in cold stores. Introduction of microtubes into a cold store and subsequent removal of selected microtubes is usually automated.

A variety of existing technology is available for the handling of microtubes. It is an object of the present invention to provide for a new, alternative, method and apparatus for automated handling of compound storage vessels.

SUMMARY OF THE INVENTION

According to a first aspect of the present invention there is provided a method of handling a compound storage vessel disposed in a cavity in a rack, the cavity having an upper opening and a lower opening, the method comprising the step of introducing a lifting pin into the cavity through the lower opening to urge the compound storage vessel upwards within the cavity.

According to a second aspect of the present invention there is provided apparatus for handling a compound storage vessel disposed in a cavity in a rack, the cavity having an upper opening and a lower opening, the apparatus comprising a lifting pin and associated actuator, the lifting pin being arranged to be inserted into the cavity through the lower opening and operable by means of the actuator to urge the compound storage vessel upwards within the cavity.

Using a lifting pin enables individual compound storage vessels to be selected and raised within a rack.

In one embodiment the method is for removing a selected vessel or vessels from a rack and further comprises the step of locating a lifting head defining at least one cavity over the rack so that the at least one cavity is aligned with the cavity in the rack containing the selected vessel, raising the selected vessel out of its cavity in the rack by means of the lifting pin so that the vessel is introduced into the cavity in the lifting head such that the vessel becomes retained relative to the lifting head.

The lifting head and rack may then be moved apart and the lifting head placed over another rack such that the cavity or cavities in the lifting head containing selected vessels are aligned with cavities in the other rack. The or each vessel retained in the lifting head may then be displaced from the lifting head into the one or more cavities in the rack. The or each vessel is preferably arranged to be retained within a cavity of the receiving head by means of a friction fit. To facilitate this one or more barbs or other projections may be disposed on the outside of each vessel. In another embodiment engageable formations are formed respectively on the outside of a vessel and the inside of the or each cavity of the lifting head to facilitate releasable engagement of the or each vessel in the or each cavity.

To facilitate transfer of vessels between the lifting head and cavity the upper opening of each cavity in the rack and/or the lower opening of each cavity in the lifting head may be flared. That is to say that the opening is of a larger cross-section than the remainder of the cavity. Likewise one or both ends of each storage vessel may be tapered.

In another embodiment the method of handling is a method of sealing a vessel and the step of raising the vessel from the rack involves bringing the top of the vessel into contact with a sheet of sealing material thereby to seal the vessel.

The sealing material may be a foil and may be coated with a heat activable polymer. In the latter case the material is preferably placed under a heated plate so that when the vessel is urged against the sheet material the material becomes sandwiched between the vessel and the plate, heating the material and melting the polymer.

Prior to contacting the sealing material the vessel is preferably urged through an aperture in a die plate disposed between the rack and sheet of material. The size of the aperture in the die plate preferably closely corresponds to the size of the vessel. Subsequent to sealing of the vessel a punch may used to displace the vessel back through the die plate into its cavity in the rack thereby cutting the sealing material around the vessel. Thus both sealing and cutting is effected by a single piece of apparatus.

BRIEF DESCRIPTION OF THE DRAWINGS

In order that the invention may be more clearly understood embodiments thereof will now be described, by way of example, with reference to the accompanying drawings of which.

DETAILED DESCRIPTION OF EMBODIMENTS OF THE INVENTION

Figure 1:
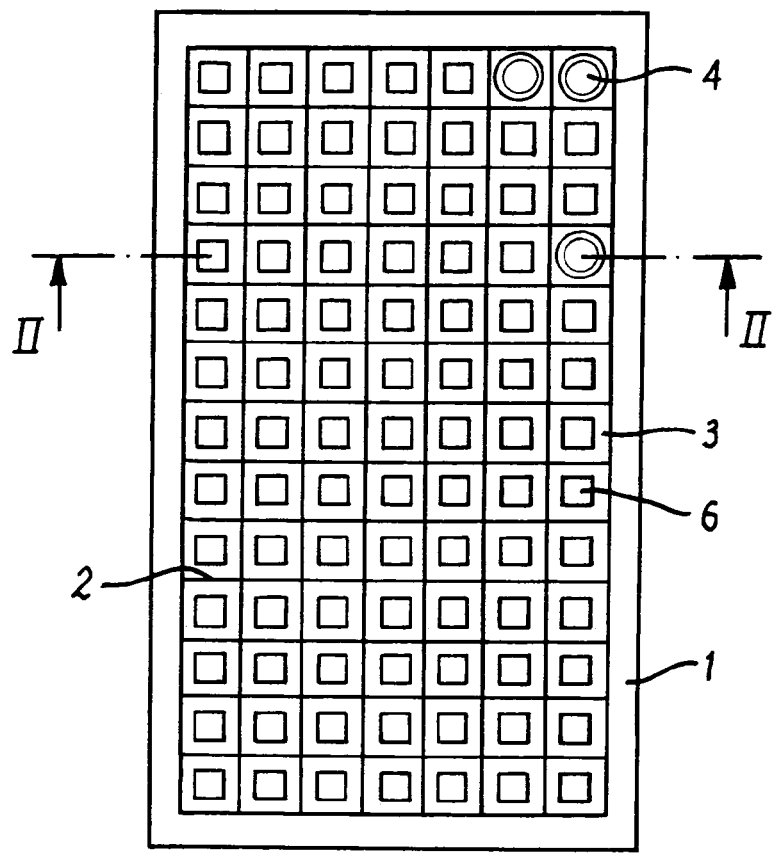
FIG. 1 is a plan view of a microtube rack.
Figure 2:
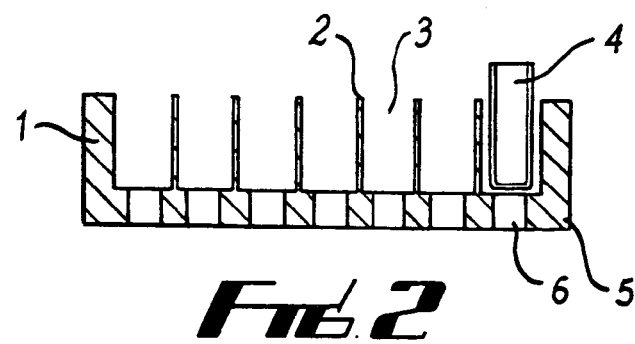
FIG. 2 is a cross-sectional view of the rack of FIG. 1, taken along line II-II.

The microtube rack of FIGS. 1 and 2 comprises a substantially rectangular outer peripheral wall 1. Within the outer wall, inner walls 2 extend between the outer walls forming a grid which defines a plurality of cavities 3 each for receiving a microtube 4. Each cavity 3 is substantially square in cross-section.

The inner walls 2 of the illustrated rack define a grid of seven by thirteen cavities 3. However, any number of cavities may be defined, as desired or as appropriate. Typically, industry standard racks define 96, 384 or 1356 cavities.

Microtubes 4 are shown in three of the cavities of the illustrated rack.

As used herein the terms upper, lower, top, bottom and like terms are used in relation to the rack as illustrated, oriented as it would be in normal use.

To the top of the microtube rack each cavity 3 is open enabling microtubes to be introduced into and removed from each cavity 3 from the top of the rack. The inner walls 2 become thinner towards the top of each cavity 3 to facilitate entry of microtubes into the cavity. The opposite end of each cavity, towards the bottom of the rack, is partially closed by a perforated base plate 5. The base plate 5 forms the underside of the rack and defines a respective aperture 6 corresponding to each cavity 3. Each aperture 6 is of a smaller cross-section than its associated cavity 3, sufficiently small to prevent a microtube 4 passing through the aperture 6, whilst allowing access to the bottom of a microtube 4 disposed in the cavity 3 from the underside of the rack.

Other embodiments of the rack are possible provided that the microtube 4 may be introduced into and withdrawn from a cavity 3 from above the rack, retained in the cavity and accessed from the underside of the rack. In one embodiment the base plate 5 is omitted and each microtube provided with a peripheral projecting lip towards the top end of the tube, the lip projecting sufficiently to prevent it entering a cavity in the rack and therefore to prevent the microtube passing right through the cavity. In another embodiment each microtube is arranged to engage with the inside of a cavity. In one arrangement each microtube is sufficiently large so that it will engage with an interference friction fit with each cavity, in another arrangement a formation is provided on the outside of each microtube and/or the inside of the cavity such that the microtubes engage with the cavities.

Embodiments of the present invention provide for sealing of microtubes 4 disposed in a rack of the types discussed above and other embodiments provide for the removal of microtubes 4 from such a rack, and transfer to another rack.

In practice a microtube rack is supplied fully populated with empty microtubes. A user fills the microtubes with samples to be stored using a pipetting device. The microtubes are then sealed with foil and the rack put into cold storage along with other such racks.

Later it is often desired to retrieve selected microtubes from storage. This typically involves removing some, but not all, microtubes from a number of different racks. Conveniently all microtubes of interest are placed into another rack, which can then be removed from cold storage.

Figure 3:
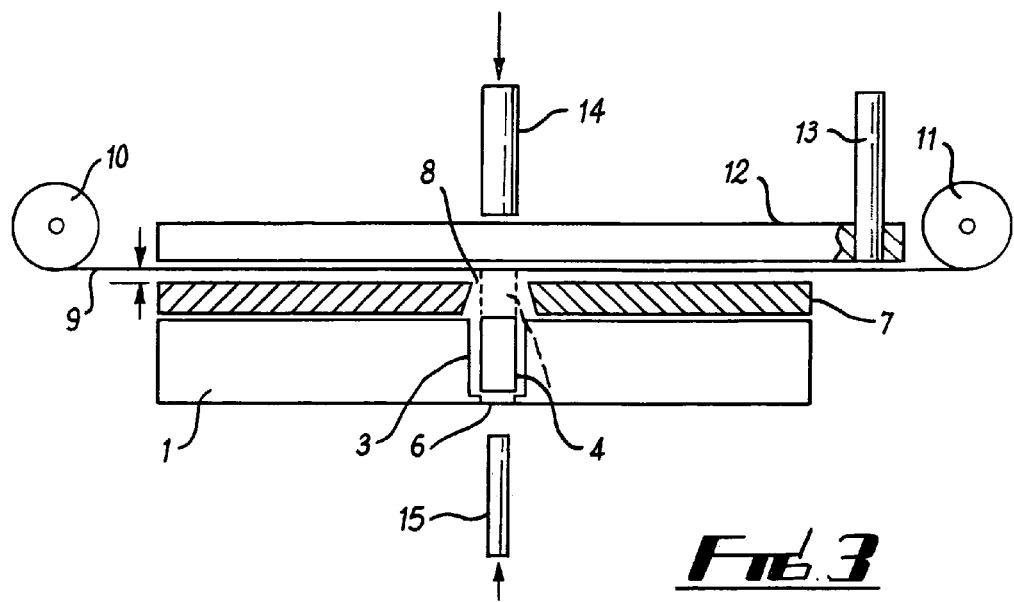
FIG. 3 is a schematic view of apparatus for sealing microtubes disposed in the rack of FIGS. 1 and 2 with foil.

FIG. 3 shows automated apparatus for sealing microtubes disposed in a rack of the type shown in FIGS. 1 and 2 with foil.

In use a rack is brought into alignment with a die plate 7. The die plate 7 defines a plurality of substantially circular apertures 8, one corresponding to each of the cavities 3 of the rack. For clarity only one aperture 8 is shown, and the rack is shown cut-away to reveal a single cavity 3 in a corresponding position to the aperture 8. A microtube 4 is disposed in the revealed cavity 3.

A layer of polymer coated foil 9 for sealing the microtubes 4 extends generally parallel with and spaced above the top surface of the die plate 7. The layer of foil 9 extends from a take-off roll 10 to a take-up roll 11. Spaced slightly above and generally parallel with the sheet of foil 9 is a heated stripper plate 12. The stripper plate 12 is pivotally mounted about an axis 13 so that it may be pivoted away from the microtube rack. Alternative ways of mounting the stripper plate are possible so that it can be moved away from the microtube rack, for example a sliding mounting. Disposed above the stripper plate 12 are a plurality of mechanically actuated punches one corresponding to, and aligned with, each aperture 8 in the die plate 7. For clarity only a single punch 14 is illustrated. Below the rack are disposed a plurality of lifting pins 15 one corresponding to and aligned with each cavity 3 of the rack. Again only one is shown, for clarity. The lifting pins 15 are sized so that they may be introduced into a cavity 3 of the rack through the corresponding aperture 6 in the base plate of the rack. The lifting pins 15 are each mounted on individually operable actuators (not shown) operative to introduce and withdraw them from the rack. In an alternative embodiment a single actuator is arranged to operate all of the pins simultaneously.

To seal a particular microtube 4 a lifting pin 15 is introduced into the cavity 3 containing the microtube 4 from below to move the microtube upwardly out of its cavity, through the corresponding aperture 8 in the die plate 7 and into contact with the foil layer 9 such that the foil layer is tightly sandwiched between the top surface of the microtube 4 and the heated stripper plate 12. The heated stripper plate 12 heats the foil 9 where it contacts the plate, activating a layer of adhesive disposed on the lower side of the foil and adhering the foil to the top of the microtube 4, thus sealing the microtube 4. Once all microtubes in a given rack that it is desired to seal have been brought into contact and adhered to the foil the lifting pins 15 are lowered. The tubes remain adhered to the foil and are thus now suspended from the foil and extend through the die plate 7. The heated stripper plate 12 is then pivoted away from the rack to expose the foil layer 9 over the die plate 7 and relevant punches 14 are then moved towards and into the apertures 8 in the die plate cutting the foil around each microtube 4 and pushing each microtube 4 back into its respective cavity 3 in the microtube rack. The punches then retract and the foil is advanced, the now perforated foil 9 being taken up by the take-up roll 11 and a new layer of foil being withdrawn from the take-off roll 10 ready for another sealing operation.

The apparatus enables individual microtubes in a rack to be sealed, and it is found that by bringing tubes individually into contact with the foil a better seal is obtained than with the prior art methods.

Figure 4:
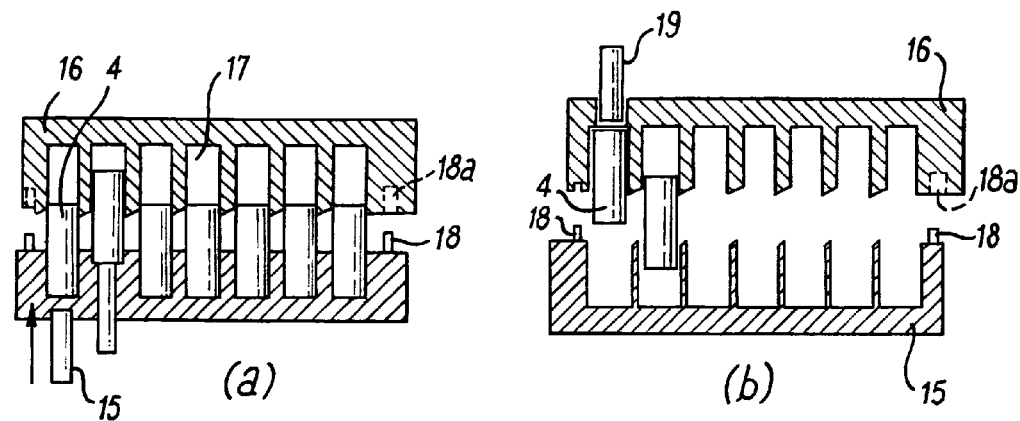
FIG. 4 shows the schematic view of apparatus for removing selected microtubes from one rack and transferring them to another.

FIG. 4 shows apparatus for picking one or more microtubes from a rack thereof and transferring them into another rack.

The picking operation is labelled "a". A picking head 16 is placed on top of a rack. The picking head defines a number of cavities 17 open on their underside. These cavities are spaced in a corresponding way to those of the rack, but in contrast to those of the rack are narrower such that microtubes inserted into the cavities are retained with a friction fit. The picking head 16 is aligned with the rack so that each cavity in the picking head is aligned with a corresponding cavity in the rack. To facilitate alignment mutually engageable formations are provided on the rack and picking head respectively for example, projections 18 on the rack (such as a dowel) are arranged to be received into corresponding apertures 18a on the picking head 16.

Once the picking head has been aligned with the rack, microtubes 4 desired to be removed from the rack are urged upwards out of their cavities in the rack and into the corresponding cavity on the picking head by means of one or more actuator operated lifting pins 15 disposed beneath the rack. The lifting pins 15 are then withdrawn.

When the chosen microtubes 4 have been transferred to the picking head 16 the picking head is lifted off the rack and moved to a receiving rack, taking the chosen microtubes with it. This is illustrated at "b". The picking head 16 is aligned with the receiving rack so that the cavities of the picking head are each aligned with a cavity of the receiving rack. The microtubes 4 disposed in the cavities of the picking head are now transferred to the receiving rack by the use of pins 19 (only one of which is shown) introduced into the picking head from above and operative to urge the microtubes 4 out of the cavities 17 in the picking head 16.

The picking head may be mounted on a robotic arm (not shown), as may the or each lifting pin 15 and pin(s) 19. The picking head 16 need not define as many cavities 17 as a microtube rack and a lifting pin 15 need not necessarily be provided for each cavity. Rather, in one embodiment, a picking head is provided which defines fewer cavities than a microtube rack and it is indexed along a microtube rack to enable selected microtubes to be removed from the rack. The lifting pin or pins may also be mounted on a robotic arm, preferably the same arm as the lifting head. The same pins may be used to displace microtubes from the microtube rack and the picking head by moving the pins from below the rack to above the lifting head as appropriate.

The above embodiments are described by way of example only. Many variations are possible without departing from the invention.

The invention claimed is:

1. Apparatus for handling a compound storage vessel disposed in a cavity in a rack, the cavity having an upper opening and a lower opening, the apparatus comprising a lifting pin, the lifting pin being arranged to be inserted into the cavity through the lower opening and operable to urge the compound storage vessel upwards within the cavity, the apparatus further comprising a sheet of sealing material comprised of foil and arranged such that the compound storage vessel may be moved upwards within the cavity by the lifting pin to bring a top of the compound storage vessel into contact with the sheet of sealing material, thereby sealing the compound storage vessel.

2. Apparatus as claimed in claim 1 further comprising a heating plate positioned above the sheet of sealing material such that when a compound storage vessel is brought into contact with the sheet of sealing material it brings the sealing material into contact with the heating plate so that the sealing material becomes sandwiched between the compound storage vessel and the heating plate.

3. Apparatus as claimed in claim 2 further comprising a die plate having at least one aperture and positioned beneath the sheet of sealing material, such that a compound storage vessel is moved through an aperture in the die plate and into contact with the sheet of sealing material.

4. Apparatus as claimed in claim 3 further comprising a punch positioned above the die plate and arranged to be moved downwards through an aperture in the die plate.

5. Apparatus for handling a compound storage vessel disposed in a cavity in a rack, the cavity having an upper opening and a lower opening, the apparatus comprising a lifting pin, the lifting pin being arranged to be inserted into the cavity through the lower opening and operable to urge the compound storage vessel upwards within the cavity, the apparatus further comprising a sheet of sealing material which comprises an adhesive arranged such that the compound storage vessel may be moved upwards within the cavity by the lifting pin to bring a top of the compound storage vessel into contact with the sheet of sealing material, thereby sealing the compound storage vessel.

6. Apparatus for handling a compound storage vessel disposed in a cavity in a rack, the cavity having an upper opening and a lower opening, the apparatus comprising a lifting pin, a heating plate positioned above the lifting pin and a sheet of sealing material comprised of an adhesive disposed between the lifting pin and the heating plate, the lifting pin being arranged to be inserted into the cavity through the lower opening to urge the compound storage vessel upwards within the cavity to bring the top of the compound storage vessel into contact with the sheet of sealing material so that the sealing material becomes sandwiched between the compound storage vessel and heating plate to heat the sheet of sealing material and adhere it to the top of the compound storage vessel, thereby sealing the compound storage vessel.

* * * * *